United States Patent [19]

Nippoldt et al.

[11] Patent Number: 4,798,197

[45] Date of Patent: Jan. 17, 1989

[54] SAFETY FEATURES FOR CONTINUOUS MOTION THERAPY SYSTEM

[75] Inventors: Robert H. Nippoldt, Newport; Gary A. Rocheleau, Maple Grove, both of Minn.; Thomas C. Wright, Longmont, Colo.

[73] Assignee: Empi, Inc., Fridley, Minn.

[21] Appl. No.: 24,232

[22] Filed: Mar. 10, 1987

[51] Int. Cl.$^4$ .............................................. A61H 1/02
[52] U.S. Cl. .............................. 128/25 R; 128/423 W
[58] Field of Search ........................ 128/25 R, 423 W

[56] References Cited

U.S. PATENT DOCUMENTS

| | | | |
|---|---|---|---|
| 4,509,509 | 4/1985 | Bouvet et al. | 128/25 R |
| 4,520,827 | 6/1985 | Wright et al. | 128/423 |
| 4,549,534 | 10/1985 | Zagorski et al. | 128/25 |
| 4,558,692 | 12/1985 | Greiner | 128/25 R |
| 4,566,440 | 1/1986 | Berner et al. | 128/25 |
| 4,621,620 | 11/1986 | Anderson | 128/25 R |

Primary Examiner—Leo P. Picard
Attorney, Agent, or Firm—Kinney & Lange

[57] ABSTRACT

Safety features for a continuous motion therapy system of the type including a carriage for supporting a patient's limb, a drive unit for driving the carriage through a range of reciprocal angular movement, first and second channel neuromuscular stimulators for applying electrical stimulation to muscles of a patient's limb, and a controller for controlling the drive unit and stimulators. Both stimulator channels must be turned OFF after the controller is powered up before either stimulator channel will operate. The drive unit is enclosed by a cover. When pressure on the cover is sensed, the controller stops and reverses the direction of the carriage. The drive unit includes a drive motor which is coupled to the carriage by a linkage. Limit switches provide limit signals when the linkage reaches predetermined limit positions. In response, the controller stops and reverses direction of the carriage. A remote patient controller which is coupled to the controller by a multi-conductor cable permits the patient to control motion of the carriage from a remote location. Should the cable be disconnected from the controller, or should any lead therein become open or short circuited, the controller causes motion of the carriage to stop either immediately or after the remote patient controller is again actuated.

24 Claims, 9 Drawing Sheets

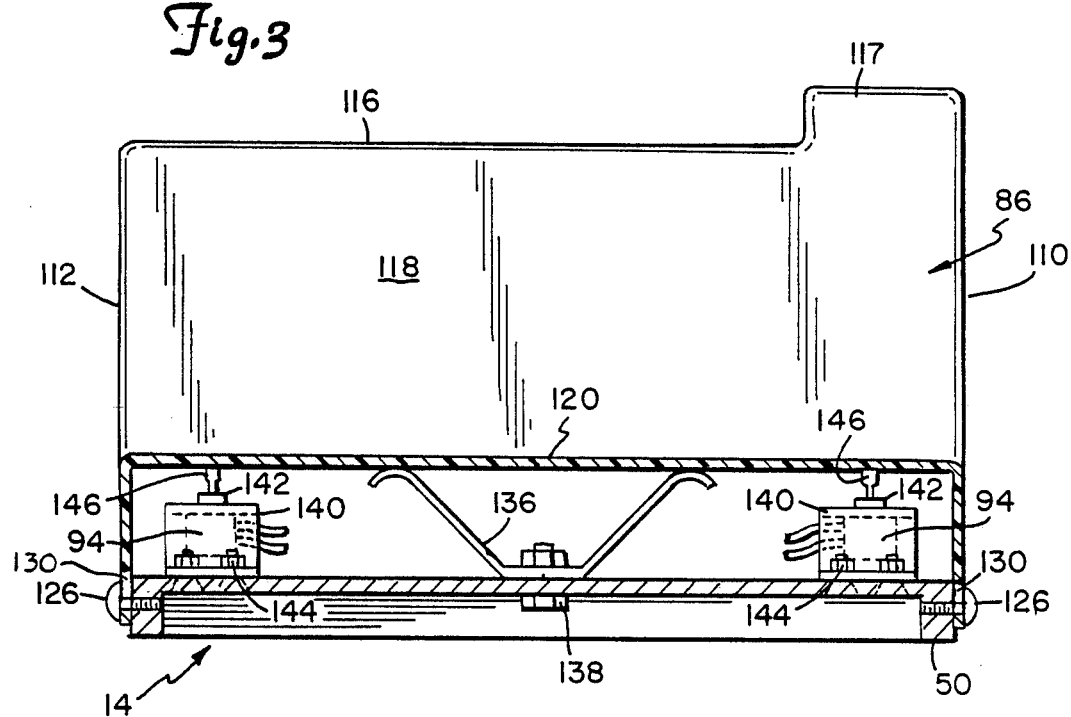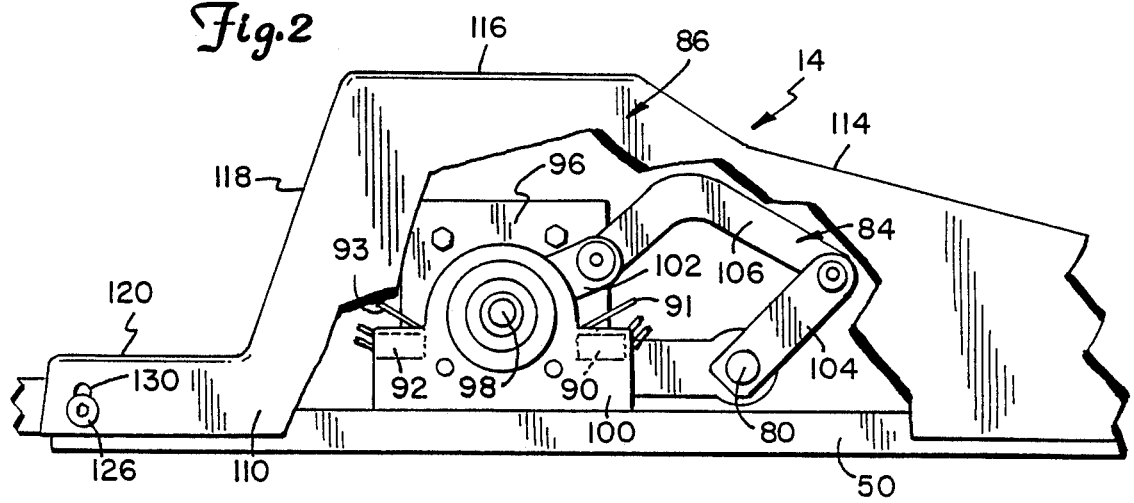

SAFETY FEATURES FOR CONTINUOUS MOTION THERAPY SYSTEM

BACKGROUND OF THE INVENTION

1. Field of the Invention

The present invention relates to continuous motion therapy systems. In particular, the present invention relates to safety features for a continuous motion therapy system.

2. Description of the Prior Art

In recent years there has been an increasing awareness of the advantages of mobilization of joints as part of the orthopedic care which follows an injury, an illness or surgical procedure. A joint can stiffen rapidly as a result of immobilization, and in many cases, extensive therapy is required in order to regain full use of a joint after it has stiffened.

Active motion of a joint occurs when the patient has sufficient muscle strength to flex or extend the limb without the need for external applied force. In contrast, passive motion of a joint involves the use of an external force to flex and extend the limb to induce motion. Continuous passive motion of a joint following injury, illness or surgery has been found to reduce post-operative pain, decreased adhesions, decreased muscle atrophy, and enhance the speed of recovery, while minimizing other risks of immobilization such as venous stasis, thromboembolism and post-traumatic osteopenia.

Continuous motion systems for providing continuous motion therapy are known and commercially available. One such system is disclosed in the Berner et al. U.S. Pat. No. 4,566,440. It is also known to aid the continuous motion provided by the systems with neuromuscular stimulation (NMS). A system of this type is disclosed in Wright et al. U.S. Pat. No. 4,520,827. Continuous motion systems such as the types discussed above have proven to be both safe and effective. There is, however, always room for additional safety features.

SUMMARY OF THE INVENTION

The present invention is a continuous motion system for providing continuous motion therapy to a patient's limb. A first embodiment of the system includes a carriage for supporting a patient's limb, drive means for driving the carriage through a range of reciprocal angular movement, and neuromuscular stimulation means for applying electrical stimulation to muscles of a patient's limb. Control means control the drive means and the neuromuscular stimulation means. The control means include ON/OFF switch means having ON and OFF states for controlling the application of power to the control means. NMS switch means have ON and OFF states, and control the NMS means. NMS safety circuit means coupled to the on/off switch means, the NMS switch means, and the NMS means disable the NMS means and thereby prevent the application of electrical stimulation when the ON/OFF switch means is in its ON state until after the NMS switch means has been switched from its OFF state to its on state.

A second embodiment of the present invention includes a carriage for supporting a patient's limb, drive unit means for driving the carriage through a range of reciprocal angular movement by cyclically driving the carriage in a first direction toward an extension end position and in a second direction toward a flexion end position. Obstruction sensor means sense obstructions with respect to the carriage. Control means responsive to the obstruction sensor means control the drive unit.

In a third embodiment, the continuous motion system includes a carriage for supporting a patient's limb, drive unit means for driving the carriage through a range of reciprocal angular movement, and a remote patient controller switch. First ends of a plurality of conductors of a remote patient controller cable are interfaced to the remote patient controller switch. Second ends of conductors of the remote patient controller cable are interfaced to control means. The control means control the drive unit means as a function of patient actuation of the remote patient controller switch and cause motion of the carriage to stop when some of the conductors of the remote patient controller cable are open circuited. In other embodiments, a control means causes motion of the carriage to stop when some of the conductors of the remote patient control cable are short circuited.

In yet another embodiment, the continuous motion system includes a carriage for supporting a patient's limb, drive unit means for driving the carriage through a range of reciprocal angular movement, and a remote patient controller switch. The remote patient controller switch is interfaced through a plurality of conductors of the remote patient controller cable to a plug connector. Control means which includes a jack adapted to receive the plug connector control the drive unit means as a function of patient actuation of the remote patient controller switch. The control means cause motion of the carriage to stop when the plug connector is unplugged from the jack.

BRIEF DESCRIPTION OF THE DRAWINGS

FIG. 2 is a side view of the drive unit shown in FIG. 1, with portions broken away to illustrate the drive motor and limit switches.

FIG. 3 is a view of the drive unit shown in FIG. 1, with portions thereof broken away to illustrate the cover sensing circuitry.

DETAILED DESCRIPTION OF THE PREFERRED EMBODIMENTS

System 10 Overview

Figure 1:
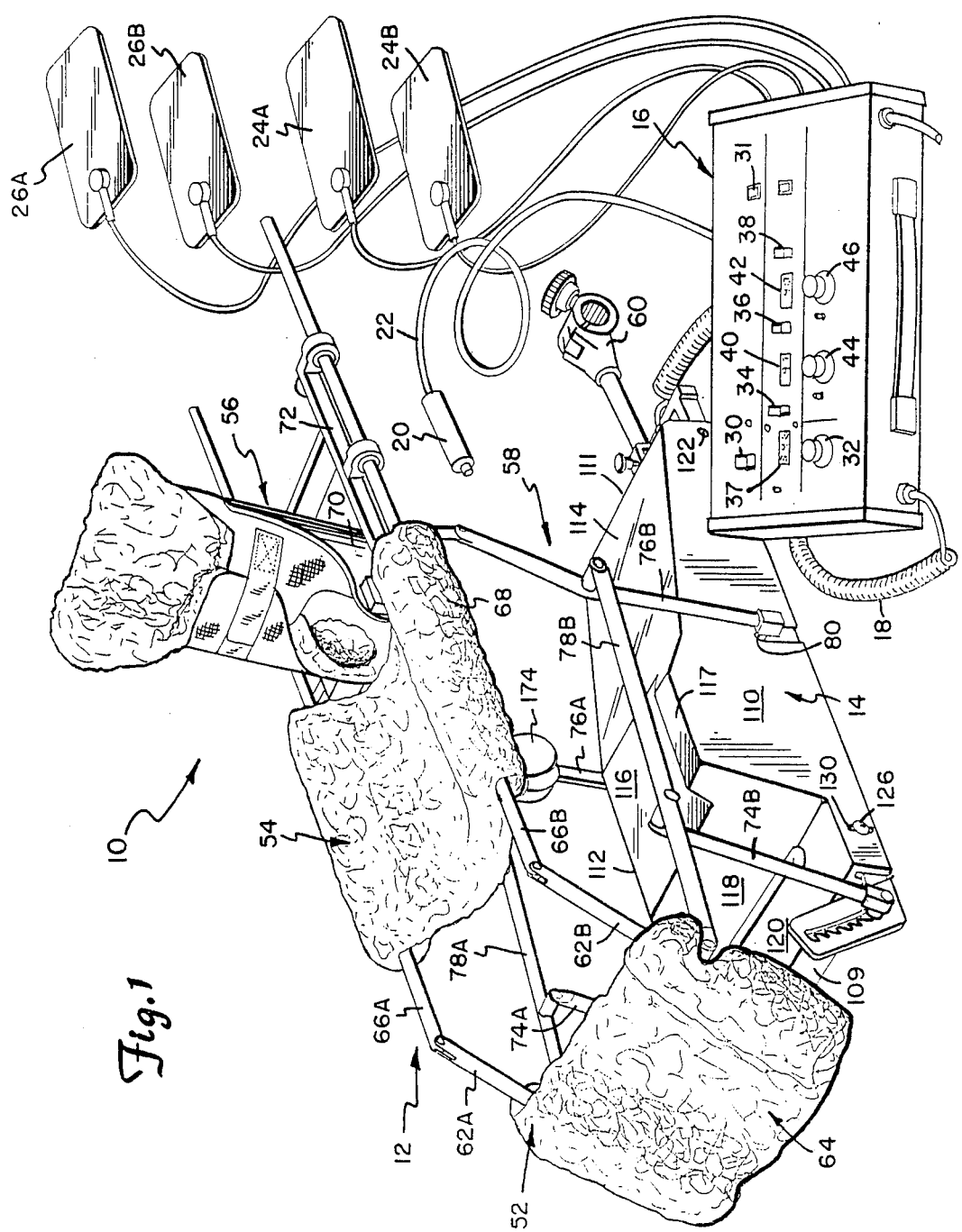
FIG. 1 is a view illustrating components of a continuous motion system which includes the safety features in accordance with the present invention.

A continuous motion therapy system 10 in which safety features of the present invention can be incorporated as illustrated generally in FIG. 1. Motion therapy system 10 includes a carriage 12 for supporting a patient's leg (not shown). Carriage 12 is driven in a reciprocal fashion between a flexion end position and an extension end position by drive unit 14. Operation of drive unit 14 is controlled by main controller 16 through drive unit cable 18. A patient can cause carriage 12 to start moving in one direction, stop, move in the other direction, stop, etc., through successive actuation of START/STOP switch 31. A patient can also remotely control the operation of system 10 in a similar manner through remote patient controller 20 which is coupled to controller 16 through remote controller cable 22. Controller 16 also includes dual channel neuromuscular stimulation or "NMS" apparatus for providing electrical stimulation to the patient's quadraceps muscle. Channel 1 NMS is applied to the patient's muscles through electrodes 24A and 24B, while channel 2 NMS is applied through electrodes 26A and 26B.

Other than through actuation of remote patient controller 20, a patient, therapist or other operator controls and monitors the status of motion therapy system 10 through main controller 16. Controller 16 is turned on or "powered up" by actuation of main power or ON/OFF switch 30. The speed at which carriage 12 is driven between its extension and flexion end positions is set by carriage speed control 32. Using display select switch 34, the operator can obtain a visual readout from display 37 of either the elapsed time that system 10 has been running, or the total number of carriage cycles which have been completed. The flexion end position is selected and set by the operator through actuation of flexion end position select switch 36. An extension end position is similarly selected and set through actuation of extension end position select switch 38. Displays 40 and 42 provide a visual display of selected flexion and extension end positions, respectively. Channel 1 NMS is enabled and its intensity controlled by NMS1 ON/OFF and intensity control switch 44. Similarly, channel 2 NMS is enabled and its intensity controlled by NMS2 ON/OFF and intensity control switch 46.

The general operation of motion therapy systems such as 10 is well known. Controller 16 controls drive unit 14 in such a manner as to cause carriage 12 to move the patient's leg in a reciprocal manner between selected flexion and extension end positions. The flexion end position is the position at which the angle between a femur and tibia of the patient's leg is at a maximum. The extension end position is the position at which the angle between the femur and tibia is at a minimum. Motion of the carriage as it is being driven from the flexion to the extension end position is characterized as motion in the forward direction. Carriage motion when being driven from the extension end position to the flexion end position is characterized as motion in the reverse direction. The position or state of carriage 12 when driven to its maximum extension position is characterized as 0°. Using this reference, carriage 12 can be driven to a maximum flexion position of 115° in the embodiment described in subsequent portions of this specification. Apparatus for setting these positions is described in applicant's copending application entitled LIVE DISPLAY APPARATUS FOR SETTING EXTENSION AND FLEXION LIMITS IN CONTINUOUS PASSIVE MOTION (CPM) SYSTEM. Filed on Dec. 20, 1985 and assigned Ser. No. 811,636.

The application of NMS is coordinated with the position or state of carriage 12. Typically, controller 16 will cause the carriage 12 to pause at its extension end position, and to then apply NMS to the patient's leg to complete leg extension to prevent dasuse atrophy and extend range of motion. A system of this type is disclosed, for example, in the Wright et al. U.S. Pat. No. 4,520,827.

Motion therapy system 10 includes a number of features which help ensure safe, comfortable, and effective rehabilitation of the patient's leg. To prevent accidental application of NMS to the patient's legs, both NMS1 and MNS2 ON/OFF and intensity control switches 44 and 46, respectively, must be turned to their OFF position before NMS can be applied through either channel. Apparatus is included to sense obstructions between carriage 12 and drive unit 14. Should any such obstructions be sensed, controller 16 stops and reverses the direction in which carriage 12 is being driven so as to release the obstruction. Should drive unit cable 18 be disconnected from either drive unit 14 or controller 16, or should individual leads within the cable break or open circuit, motion of carriage 12 is stopped. Motion of carriage 12 is also stopped either immediately or after actuation of remote patient controller 20 if stop cable 22 is disconnected from controller 16, or if any wire therein is open or short circuited. Controller 16 also reverses the direction of carriage 12 should the carriage drive unit exceed predetermined extension or flexion limits.

Carriage 12 and Drive Unit 14

Carriage 12 and drive unit 14 are described generally with reference to FIGS. 1–3. Carriages such as 12 are known and disclosed, for example, in the Berner et al. U.S. Pat. No. 4,566,440. As shown, carriage 12 includes a base or frame 50, femur support 52, tibia support 54, foot support 56, double four-bar support linkage 58 and bed connector 60. Femur support 52 includes a pair of parallel femur support tubes 62A and 62B, and a U-shaped flexible thigh support saddle 64. Tibia support 54 is formed by a pair of tibia support tubes 66A and 66B, and a calf support saddle 68. Foot support 56 includes a foot bed 70 which is adjustably mounted to tubes 66A and 66B by foot bed mounting assembly 72.

Femur support 52 and tibia support 54 are supported and guided in their movements with respect to one another and with respect to frame 50 by double four-bar linkage 58. In the embodiment shown in FIG. 1, linkage 58 includes a pair of parallel rear support links 74A and 74B, a pair of forward support links 76A and 76B, and a pair of parallel drag links 78A and 78B. Forward support links 76A and 76B have their lower ends connected to opposite ends (only one is shown) of transverse tube 80 which is pivotally mounted with respect to frame 50.

Figure 4:
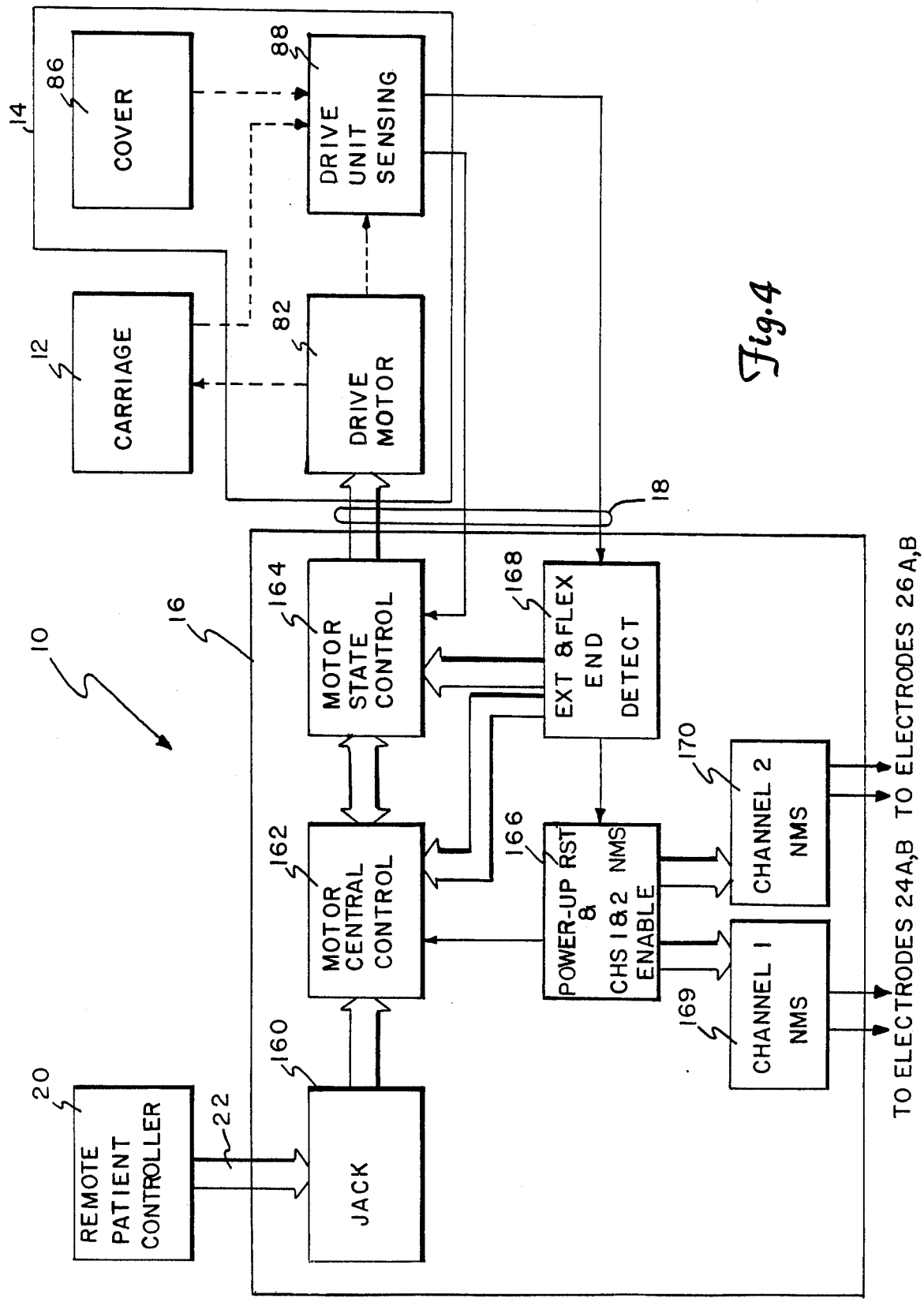
FIG. 4 is a block diagram representation of the system shown in FIG. 1, illustrating in detail various circuit elements of the controller.

Drive unit 14 includes a drive motor 82 (not visible in FIGS. 1–3), drive linkage 84, drive unit cover 86, and drive unit sensing circuitry 88 (FIG. 4) which includes extension limit switch 90, flexion limit switch 92, cover sensing switches 94 (two are shown in FIG. 3) and carriage state or position sensor 174. Motor 82 is mounted to frame 50 by motor mount bracket 96 and has a drive shaft 98 which is pivotally mounted with respect to frame 50 by bracket 100. Linkage 84 includes first crank arm 102 which is fixedly mounted to shaft 98 of motor 82, a second crank arm 104 which is fixedly mounted to transverse tube 80, and a connecting link 106 which is pivotally coupled to crank arms 102 and 104. As illustrated in FIG. 4, drive motor 82 is interfaced to controller 16 and in response to drive signals therefrom causes crank 102 to reciprocally rotate in both clockwise and counterclockwise directions. This rotational motion is coupled by linkage 84 to transverse tube 80, and thereby reciprocally drives carriage 12 between its extension and flexion end positions.

Extension limit switch 90 is mounted with respect to bracket 100 in such a manner that its actuator arm 91 will be actuated by crank arm 102 should motor 82 attempt to drive carriage 12 beyond a predetermined extension limit. Flexion limit switch 92 is mounted with respect to bracket 100 in such a manner that its actuator arm 93 will be actuated by crank arm 102 should motor 82 attempt to drive carriage 12 beyond a predetermined flexion limit position. The extension and flexion limit positions are determined by the relative position of actuator arms 91 and 93, respectively, with respect to crank arm 102. Although not illustrated in FIG. 2, switches 90 and 92 are coupled to controller 16 through drive unit cable 18.

Motor 82, cover switches 94, limit switches 90 and 92, linkage 84, and other structural and electrical elements are enclosed by cover 86. As perhaps best shown in FIG. 1, cover 86 includes side panels 110 and 112, end panels 109 and 111, and a top panel formed by surfaces 114, 116, 118 and 120. Top panel surface 114 slopes gradually from end panel 111 to top panel surface 116. Top panel surface 116 is generally level, and positioned over motor 82. Top panel surface 116 is generally level, and includes an extended section 117 which accomodates linkage assembly 84. Top panel surface 116 slopes steeply from surface 118 to surface 120, while top panel surface 120 is generally level.

A first end (adjacent bed connector 60) of cover 86, the end which is adjacent end panel 111, is pivotally connected to frame 50 by pivot pins 122 (only one is shown) which extend through side panels 110 and 112. A second opposite end of cover 86 (an end adjacent top panel surface 120 or the patient end) is slidably mounted to frame 50 by pin 126 at its first side 110 adjacent linkage 84. As shown in FIGS. 1, 2 and 3, cover 86 includes a vertically elongated slot 130 through which pin 126 extends, thereby permitting pivotal motion of cover 86 about pivot pins 122, while prohibiting cover 86 from being raised. The second side 110 of cover 86 at the patient end is free moving or unattached to frame 50. The second end of cover 86 is supported by leaf spring 136 which is mounted to frame 50 by fastener 138. Leaf spring 136 is positioned to contact a lower (inside) surface of top panel surface 120 of cover 86.

Cover switches 94 are mounted to angle brackets 140 by means of a threaded nut 142. Angle brackets 140, in turn, are mounted to frame 50 by fasteners 144. Cover switches 140 are thereby mounted in a spaced apart relation from frame 50, and have actuator levers or pins 146 which contact the lower or inside surface of top panel surface 120. Although not illustrated, cover switches 94 are interfaced to controller 16 through drive unit cable 18. If pressure due to an obstruction or otherwise is applied to top panel surfaces 114, 116, 117, 118, or 120, cover 86 will pivot about pins 122 with the second end adjacent top panel surface 120 sliding downward against the force of spring 136. The inside of top panel surface 120 will then actuate pin 146 of one or both cover switches 94.

Controller 16

FIG. 4 is a block diagram representation of motion therapy system 10 illustrating control unit 16 in greater detail. As shown, control unit 16 includes plug jack 160, motor central control 162, motor state control 164, power-up reset and channels 1 and 2 NMS enable 166, extension and flexion end detection circuitry 168, channel 1 NMS 169 and channel 2 NMS 170. Controller 16 is interfaced to drive unit 14 through drive unit cable 18. As shown, drive unit 14 includes drive motor 82, cover 86 and drive unit sensing circuitry 88. Drive unit 14 is also coupled to carriage 12. The broken lines coupling drive motor 82, carriage 12, sensing circuitry 88 and cover 86 indicate a physical coupling between these elements. Controller 16 is also shown interfaced to remote patient controller 20 through cable 22.

Figure 5:
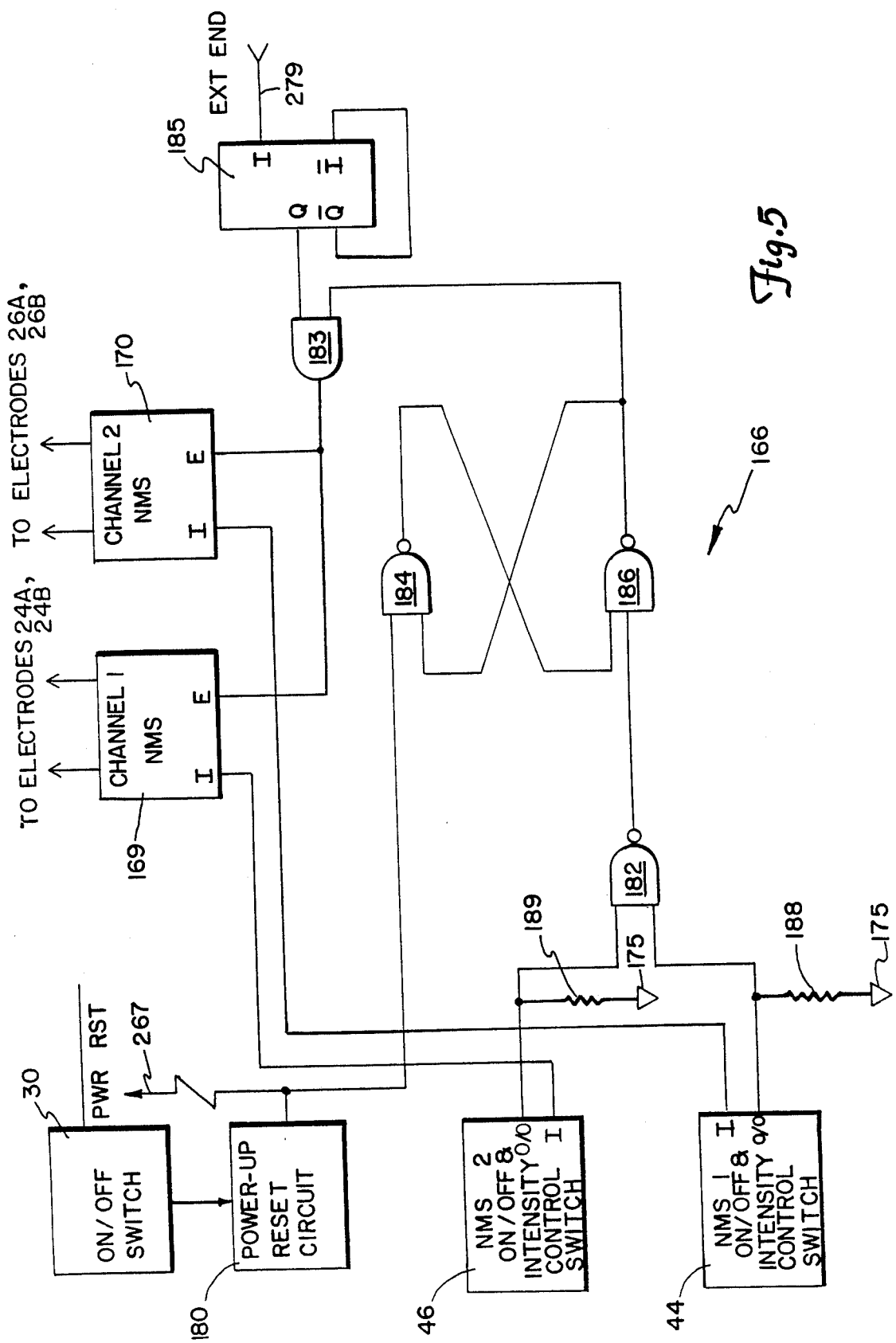
FIG. 5 is a detailed block and schematic representation of the power-up reset and NMS enable circuity shown in FIG. 4.

Power-up reset and channels 1 and 2 NMS enable circuitry 166, channel 1 NMS 169, channel 2 NMS 170 and ON/OFF switch 30 are illustrated in greater detail in FIG. 5. Power-up reset and NMS enable circuitry 166 includes power-up reset circuit 180, NMS1 ON/OFF and intensity control switch 44, NMS2 ON/OFF and intensity control switch 46, NAND gates 182, 184, and 186, AND gate 183, monostable multivibrator 185 and resistors 188 and 189. When control unit 16 is turned on by an operator through the actuation of ON/OFF switch 30, power-up reset circuit 180 produce an active low power reset signal PWR RST. The power reset signal is coupled to central control 162 over line 267, and to a first input terminal of NAND gate 184. Power-up reset circuits such as 180 are well known.

ON/OFF terminal 0/0 of switch 44 is coupled to a first terminal of NAND gate 182 and to ground 175 through resistor 188. ON/OFF terminal 0/0 of switch 46 is coupled to a second input terminal of NAND gate 182 and to ground 175 through resistor 189. An output terminal of NAND gate 182 is coupled to a first input terminal of NAND gate 186. NAND gates 184 and 186 are cross coupled to form a latch, with the output terminal of NAND gate 184 being coupled to a second input terminal of NAND gate 186, and the output terminal of NAND gate 186 being coupled to a second input terminal of NAND gate 184. The output terminal of NAND gate 186 is coupled to a first input terminal of AND gate 183. A second input terminal of AND gate 183 is connected to output terminal Q of multivibrator 185. Input terminal I of multivibrator 185 is connected to receive an extension end signal EXT END from extension and flexion end detection circuitry 168. Multivibrator 185 has its complementary output terminal $\overline{Q}$ connected to its complementary input terminal $\overline{I}$. The output terminal of AND gate 183 is coupled to an enable input terminal E of both channel 1 NMS 169 and channel 2 NMS 170.

Power-up reset and enable circuitry 166 prevents either channel 1 NMS 169 or channel 2 NMS 170 from providing NMS until both switches 44 and 46 have been switched OFF after controller 16 is initially turned ON. When switches 44 and 46 are switched to their OFF position, their on/off terminals 0/0 will be at a HIGH or logic "1" state. When switched ON, the signal at on/off terminals 0/0 of switches 44 and 46 is switched to a LOW or logic "0" state. The output terminal of NAND gate 182, and therefore the first input terminal of NAND gate 186, will be at a LOW logic state only when both switches 44 and 46 are switched OFF.

Monostable multivibrator 185 has a time constant of ten seconds in one embodiment. Upon receipt of an active high EXT END signal from extension and flexion end detection circuitry 168 indicating that carriage 12 has reached its preselected extension end position, a logic HIGH signal will be produced at output terminal q of multivibrator 185 for a time period such as ten seconds corresponding to its time constant. After this time period output terminal Q of multivibrator 185 switches to a LOW STATE.

When power is first applied to control unit 16 (i.e., ON/OFF switch 30 is switched to its ON position), and the power reset signal $\overline{\text{PWR RST}}$ is applied to the first input terminal of NAND gate 184, the latch action of NAND gates 184 and 186 causes the output terminal of gate 186 to be driven to a logic LOW state if either switch 44 or 46 is ON. The output terminal of AND gate 183 is therefore held to a logic low state also. With a logic LOW signal applied to their enable input terminal E, both channel 1 NMS 169 and channel 2 NMS 170 will be disabled, and prevented from generating NMS upon initial application of power to control unit 16.

After the initial application of power to control unit 16 and the generation of a power reset signal PWR RST by circuitry 180, channel 1 NMS 169 and channel 2 NMS 170 can be enabled only after switches 44 and 46 are first returned to their OFF position, and an EXT END signal is received from extension and flexion end detection circuitry 168. When switched to their OFF position, a logic HIGH signal is provided at the on/off terminals 0/0 of the switches 44 and 46. A logic LOW signal is therefore provided by NAND gate 182 to the first input terminal of NAND gate 186. The latching action of NAND gates 184 and 186 will cause the output terminal of NAND gate 186 to switch to a logic HIGH state. Channel 1 NMS 169 and channel 2 NMS 170 will thereby be enabled for time periods corresponding to the time constant of multivibrator 185 each time an EXT END signal is received. Channel 1 NMS 169 and channel 2 NMS 170 can then then be controlled by switches 44 and 46, respectively. In particular, either switch 44 or 46 can be switched to its ON state to activate channel 1 NMS 169 or channel 2 NMS 170, respectively. The intensity of the NMS generated is controlled by an intensity control signal provided to intensity control terminal I of channel 1 NMS 169 and channel 2 NMS 170 from intensity control terminal I of switches 44 and 46, respectively.

Figure 6:
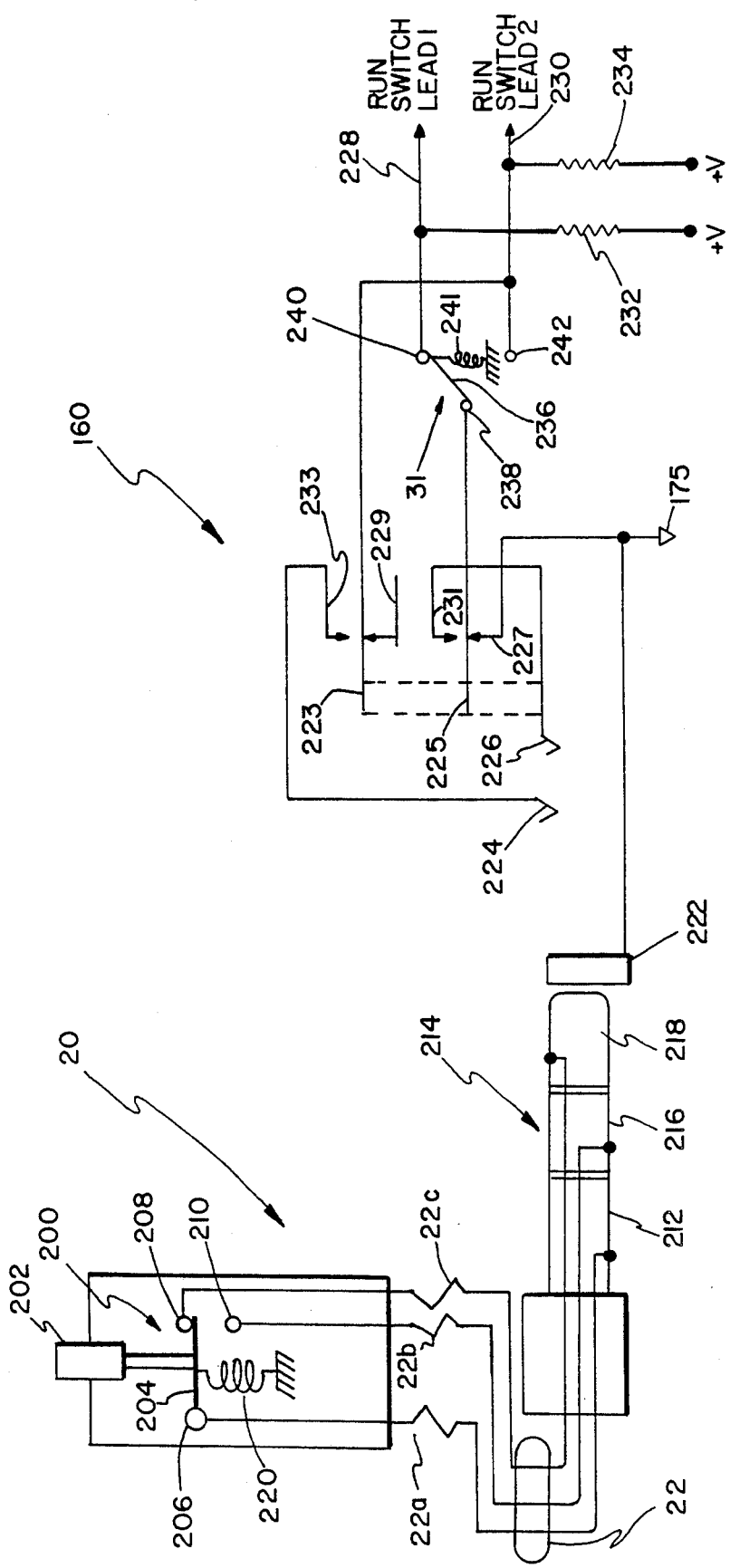
FIG. 6 is a detailed schematic diamgram of the remote patient controller and jack shown in FIG. 4.

Remote patient controller 20, jack 160 START/STOP switch 31 and their interconnections are illustrated in greater detail in FIG. 6. Patient controller 20 includes a switch 200 which is actuated by push button 202. Switch 200 includes a contact member 204, and terminals 206, 208 and 210. As shown, terminal 206 is coupled by means of wire 22a of cable 22 to base portion 212 of plug 214. Terminal 210 is coupled via wire 22b to central portion 216 of plug 214. Terminal 208 is coupled to tip portion 218 of plug 214 by wire 22c. Contact member 204 is biased by means of a spring 220 to a normally closed position electrically coupling terminals 206 and 208 when button 202 is unactuated. When switch 200 is actuated by means of button 202, contact member 204 will electrically couple terminals 206 and 210.

Jack 160 is adapted to receive plug 214 and has a base contact member 222, a central contact member 224, and a tip contact member 226. Jack 160 is coupled to a first run switch lead 228 and a second run switch lead 230 by means of START/STOP switch 31. Leads 228 and 230 are coupled to a relatively positive supply potential through pull-up resistors 232 and 234, respectively. As shown, switch 31 has a contact member 236 and terminals 238, 240 and 242. Biasing means such as spring 241 cause contact member 236 to electrically couple terminals 238 and 240 in its normally closed position when switch 31 is unactuated. When switch 31 is actuated by an operator, contact member 236 will electrically couple terminals 238 and 242.

When plug 214 is not inserted into or plugged within jack 160, tip contact 226, which mechanically actuates contact members 223 and 225, is biased to such a position that contact member 225 is electrically coupled to ground 175 through terminal 227. Contact member 223 will be floating as it is electrically coupled to terminal 229 which is not coupled to other circuit elements. First run switch lead 228 and second run switch lead 230 will therefore be at logic LOW, HIGH states, respectively, when plug 214 is not inserted into jack 160. These logic states are reversed, with logic HIGH, LOW states being present on run switch leads 228 and 230, respectively, when switch 31 is actuated.

With plug 214 inserted within jack 160, base, central and tip portions 212, 216, 218, respectively, of plug 214 will come into electrical contact with base, central and tip contacts 222, 224, 226, respectively, of jack 160. In response, tip contact 226 will force contact member 225 into electrical contact with terminal 231 and therefore contact 226. Contact member 223 is similarly forced into contact with terminal 233, and thereby central contact 224. Base contact 222 is electrically connected to ground 175.

When plug 214 has been inserted into jack 160 as described above, and switch 31 is unactuated, logic LOW, HIGH signals are present at first and second run switch leads 228 and 230, respectively. These logic states will be reversed if START/STOP switch 31 is actuated. Should switch 200 of patient controller 20 be actuated when plug 214 is plugged into jack 160, these logic states are also reversed with logic HIGH, LOW signals being presnt on run switch leads 228 and 230, respectively.

From the above description, it can be seen that the signals at run switch leads 228 and 230 will normally be at logic LOW, HIGH states, respectively, and be reversed each time START/STOP switch 31 or switch 200 of patient controller 20 is actuated. However, if plug 214 is inserted into jack 160 and either wires 22a or 22c breaks and open circuits, both run switch leads 228 and 230 will switch to a HIGH logic state. If wire 22b breaks and open circuits and switch 200 is actuated, logic HIGH signals will be present on both switch leads 228 and 230 also. If either wire 22a or 22c is short circuited to wire 22b, logic LOW signals will be present at both run switch leads 228 and 230. Logic LOW signals will also be present at both run switch leads 228 and 230 if wires 22a and 22c are short circuited, and switch 200 actuated.

Tip portion 218 of plug 214 is elongated and positioned with respect to base portion 212 in such a manner that when the plug is inserted into jack 160 or unplugged therefrom, both contacts 224 and 226 will come into electrical contact with tip portion 218 while base portion 212 is in electrical contact with base contact 222. Run switch leads 228 and 230 will therefore both be switched to a logic LOW state in the course of this plug-in or unplug action.

Figure 7:
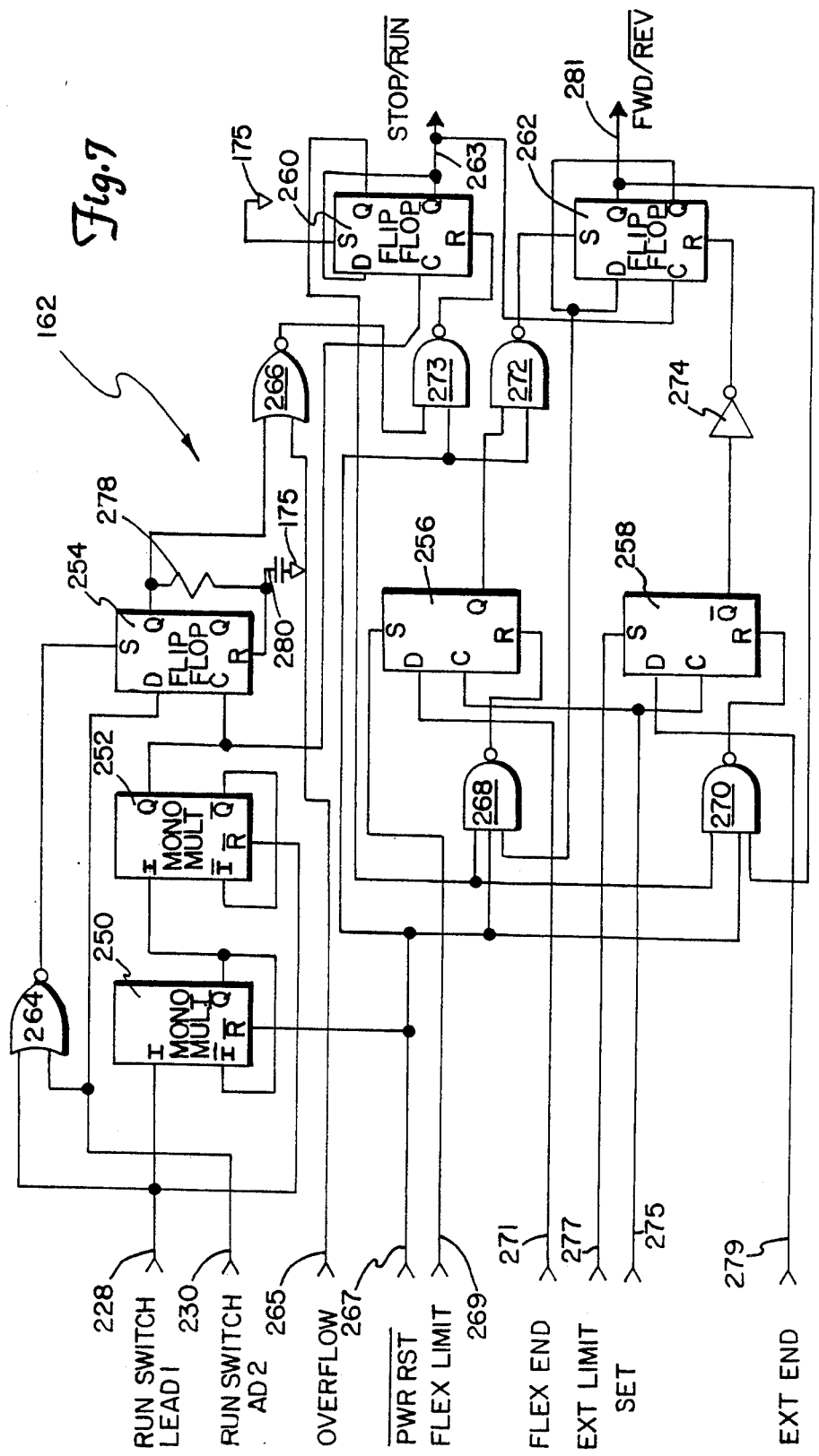
FIG. 7 is a detailed schematic diagram of the central control shown in FIG. 4.

A detailed circuit implementation of central control 162 is illustrated in FIG. 7. As shown, central control 162 includes one-shots or monostable multivibrators 250 and 252, flip-flops 254, 256, 258, 260 and 262, NOR gates 264 and 266, NAND gates 268, 270, 272 and 273 and inverter 274. Monostable multivibrator 250 has an active high input terminal I coupled to first run switch lead 228 from jack 160. An active low input terminal $\bar{I}$ is coupled to complementary output terminal $\bar{Q}$ of multivibrator 250, and to the active HIGH input terminal I of monostable multivibrator 252. An active low direct reset terminal $\bar{R}$ is connected to receive power reset signals $\overline{PWR\ RST}$ from power-up reset and enable circuitry 166. Monostable multivibrator 250 is coupled to external circuit elements (not shown) so as to have a first time constant, which is thirty-three milliseconds in one embodiment.

Monostable multivibrator 252 has its active low input terminal $\bar{I}$ coupled to its complementary output terminal $\bar{Q}$. The active low direct reset terminal $\bar{R}$ of monostable multivibrator 252 is coupled to first run switch lead 228. Output terminal Q of monostable multivibrator 252 is coupled to the positive edge triggered clock input terminal C of flip-flop 254. Monostable multivibrator 252 is connected to external circuit elements (not shown) so as to have a second time constant which is less than the first time constant of multivibrator 250. In one embodiment monostable multivibrator 252 has a one millisecond time constant.

Flip-flop 254 is connnected as a monostable multivibrator and has a data input terminal D connected to second run switch lead 230, and an active high set direct terminal S connected to an output terminal of NOR gate 264. An active high clear direct or reset terminal R of flip-flop 254 is coupled to its output terminal Q through resistor 278 and to ground 175 through capacitor 280. Values of resistor 278 and capacitor 280 are selected to have a third time constant of approximately one second. A first input terminal of NOR gate 264 is connected to first run switch lead 228, while its second input terminal is connected to second run switch lead 230.

NOR gate 266 has a first input terminal connected to the Q output terminal of flip-flop 254, and a second input terminal connected to receive an OVERFLOW signal from extension and flexion end detection circuitry 168 (FIG. 4) over lead 265. An output terminal of NOR gate 266 is connected to a first input terminal of NAND gate 273. A second input terminal of NAND gate 273 is connected to receive the $\overline{PWR\ RST}$ signal from power-up reset and enable circuitry 166 over lead 267. An output terminal of NAND gate 273 is connected to the active high reset terminal R of flip-flop 260.

Flip flop 260 produces a STOP/$\overline{RUN}$ signal at its complementary output terminal $\bar{Q}$. When the STOP/$\overline{RUN}$ signal has a HIGH logic state, motor state control 164 will cause motor 82 to break or stop. When the STOP/$\overline{RUN}$ signal has a LOW logic state, motor state control 164 will cause motor 82 to run. As shown, active high set direct terminals of flip-flop 260 is connected to ground 175. The data input terminal D of flip-flop 260 is connected to its complementary output terminal $\bar{Q}$.

NAND gate 268 has a first input terminal connected to the Q output terminal of flip-flop 260, a second input terminal connected to receive the power reset signal $\overline{PWR\ RST}$, and a third input terminal connected to the complementary output terminal $\bar{Q}$ flip-flop 262. An output terminal of NAND gate 268 is coupled to the active high reset terminal R of flip-flop 256. An active high set terminal S of flip-flop 256 is connected to receive an active high FLEX LIMIT signal from motor state control 164 over lead 269. A data input terminal D of flip-flop 256 is connected to receive an active high FLEX END signal from extension and flexion end detection circuitry 168 over lead 271. A clock input terminal C of flip-flop 256 is connected to receive an active high RESET signal from extension and flexion end detection circuitry 168 over lead 275. A complementary output terminal $\bar{Q}$ of flip-flop 256 is coupled to a first input terminal of NAND gate 272. A second input terminal of NAND gate 272 is connected to receive power reset signal PWR RST. An output terminal of NAND gate 272 is coupled to an active high set direct terminal S of flip-flop 262.

NAND gate 270 has a first input terminal connected to the Q output terminal of flip-flop 260, a second input terminal connected to receive the PWR RST signal, and a third input terminal connected to the Q output terminal of flip-flop 262. An output terminal of NAND gate 270 is coupled to the active high reset terminal R of flip-flop 258. An active high set terminal S of flip-flop 258 is connected to receive an active high EXT LIMIT signal from motor state control circuitry 164 over line 277. Flip-flop 258 has a clock input terminal C connected to receive the RESET signal, and a data input terminal D connected to receive an active high EXT END signal from extension and flexion end detection circuitry 168 over line 279. A complementary output terminal $\bar{Q}$ of flip-flop 258 is coupled to active high reset terminal R of flip-flop 262 through inverter 274.

A data terminal D of flip-flop 262 is connected to its complementary output terminal $\bar{Q}$. A clock input terminal C of flip-flop 262 is connected to receive the STOP/$\overline{RUN}$ signal from complementary output terminal $\bar{Q}$ of flip-flop 260. Flip-flop 262 produces a FWD/$\overline{REV}$ signal which is coupled from its output terminal Q to motor state control 164 over line 281. When the FWD/$\overline{REV}$ signal has a HIGH logic state, motor state control 164 causes motor 82 to drive carriage 12 in the forward direction. When the FWD/$\overline{REV}$ signal has a LOW logic state, carriage 12 will be driven in the reverse direction.

Operation of central control 162 is as follows. When power is first applied to control unit 16, the PWR RST signal generated by power-reset and NMS enable circuitry 166 (an active low pulse) will be coupled to the reset terminal R of multivibrator 250, and to NAND gates 272, 273, 268, and 270. As a result, complementary output terminals Q of multivibrator 250 and flip-flop 260 will be forced to a HIGH logic state. Drive motor 82 is thereby switched off upon initial actuation of ON/OFF switch 30 (FIG. 1). The Q output terminal (i.e., FWD/$\overline{REV}$ signal) of flip-flop 262 is also switched to its HIGH logic state to ensure motion of carriage 12 in the forward direction upon initiation of switches 200 or 31.

As previously described, when switch 200 of controller 20 and/or when START/STOP switch 31 are in their normal position (i.e., are unactuated) logic LOW, HIGH signals will be present at first run switch lead 228 and second run switch lead 230, respectively. When either switch 200 of remote patient controller 20 or START/STOP switch 31 is actuated, these logic states are reversed, with a logic HIGH signal being applied to input terminal I of multivibrator 250, and a logic LOW signal being applied to data input terminal D of flip-flop 250. As a result, complementary output terminal $\bar{Q}$ of multivibrator 250 is switched or pulsed LOW for a time period equal to its first or 33 millisecond time constant. After the 33 millisecond time period complementary output terminal $\bar{Q}$ of multivibrator 250 will switch back to a logic HIGH state. If switches 200 or 31 were truly actuated, first run switch lead 228 will still have a logic HIGH signal, with this signal still being applied to the reset terminal $\overline{R}$ of multivibrator 252. Multivibrator 252 will thereby respond to the HIGH pulse signal from multivibrator 250, causing a positive going pulse or HIGH signal to be provided at its Q output terminal. The positive going pulse at the Q output terminal of multivibrator 252 is applied to clock terminal C of flip-flop 260, causing its Q output terminal (the STOP/$\overline{\text{RUN}}$ signal) to switch to a logic LOW state, thereby enabling motor 82.

If the logic HIGH signal present at first run switch lead 228 was not caused by a true closure of one of switches 200 or 31 (e.g., if it was caused by a stray voltage spike), run switch lead 228 would return to its logic LOW state prior to the end of the 33 millisecond time period of monostable multivibrator 250, causing output terminal Q of multivibrator 252 to remain at its logic LOW state when the positive going pulse is produced at input terminal I of multivibrator 252. As a result, the Q output terminal of flip-flop 260 will not change states, and the direction of motion of motor 172 will remain unchanged. Monostable multivibrator 250 therefore functions to remove spikes which may occur from time to time on leads 228 and 230. Monostable multivibrator 252 functions to "debounce" switches 200 and 31.

From the above description, it can be seen that each time button 200 of remote patient controller 20 or run switch 31 is actuated, the logic state of the signal at the $\overline{Q}$ output terminal of flip-flop 260 (the STOP/$\overline{\text{RUN}}$ signal) will switch from either a LOW to a HIGH state and stop or inhibit motor 82, or switch from a HIGH to a LOW state, thereby enabling and permitting motor 82 to run.

As discussed above, should leads 22a-22c of cable 22 short circuit, or should plug 214 be plugged into or unplugged from jack 160, logic LOW, LOW signals will be present at run switch leads 228 and 230, respectively. Under these circumstances the output signal from NOR gate 264 and therefore the signal applied to set terminal S of flip-flop 254 will switch to a HIGH logic state. Output terminal Q of flip-flop 254 will be switched to a HIGH logic state and held HIGH for its third or one second time constant period due to the action of resistor 278 and capacitor 2SO. The logic HIGH signal at the Q output terminal of flip-flop 254 will cause reset terminal R of flip-flop 260 to be switched to a HIGH logic state, forcing the STOP/$\overline{\text{RUN}}$ signal LOW for at least one second, and stopping carriage 12.

Should leads 22a-22c open circuit, logic HIGH signals will be present at both run switch leads 228 and 230. Data input terminal D of flip flop 254 will then be at a logic HIGH state when the positive going pulse produced at output terminal Q of multivibrator 252 clocks terminal C of flip-flop 254. Output terminal Q of flip-flop 254 is thereby switched HIGH, causing the STOP/$\overline{\text{RUN}}$ signal produced by flip-flop 260 to be switched to a LOW logic state in the manner described above. Carriage 12 is thereby stopped when these failures occur.

The direction in which drive motor 82 (FIG. 4), and therefore carriage 12, is being driven is controlled by motor state control 164 (FIG. 4) in response to the FWD/$\overline{\text{REV}}$ signal provided at the Q output terminal of flip-flop 262. When carriage 12 is being driven in either its forward or reverse direction, the STOP/$\overline{\text{RUN}}$ signal at complementary output terminal $\overline{Q}$ of flip-flop 260 will be at a LOW logic state. If switch 200 of remote patient controller 20 or START/STOP switch 31 on main controller 16 is actuated, the STOP/RUN signal is switched to a logic HIGH state, clocking flip-flop 262. Since complementary output terminal $\overline{Q}$ of flip-flop 262 is coupled to its data input terminal D, this clocking causes the FWD/$\overline{\text{REV}}$ signal of output terminal Q to change states. As a result, the next actuation of switch 200 of patient controller 20 or START/STOP switch 31 will cause carriage 12 to start running in the opposite direction. Successive actuation of either switch 200 or 31 causes carriage 12 to stop, run forward, stop, run reverse, stop, run forward, etc.

When carriage 12 is being driven in its forward (toward extension) or reverse (toward flexion) directions during normal operation, the EXT LIMIT, STOP/$\overline{\text{RUN}}$ and EXT END signals will have a LOW logic state. The RESET signal received from extension and flexion end detection circuitry 168 is periodically pulsed to a LOW logic state as will be subsequently described. The $\overline{\text{PWR RST}}$ signal will be at a HIGH logic state. Flip-flop 258 will have been clocked in such a manner that its complementary output terminal $\overline{Q}$ is switched to a HIGH logic state, with inverter 274 applying a logic LOW signal to the reset terminal R of flip-flop 262. During this operation, the FLEX LIMIT and FLEX END signals will also have a logic LOW state. Flip-flop 256 will have been clocked previously in such a manner that its output terminal Q is at a HIGH logic state, with this signal being inverted by NAND gate 272 to apply a LOW logic signal to the set terminal S of flip-flop 262. With both the set terminal S and reset terminal R of flip-flop 262 at a LOW logic state, and its complementary output terminal $\overline{Q}$ coupled to its data input terminal D, the FWD/$\overline{\text{REV}}$ signal can change states in response to actuation of switch 200 of remote patient controller 20 or START/STOP switch 31 as described above.

When carriage 12 is being driven in the forward direction (towards its extension end position), and reaches its preselected extension end position, extension and flexion end detection circuitry 168 will cause the EXT END signal to switch to a HIGH logic state. The RESET signal will also switch to a HIGH logic state. Complementary output terminal $\overline{Q}$ of flip-flop 258 is thereby switched to a LOW logic state, with this signal being inverted by inverter 274 to apply a HIGH logic signal to the reset terminal R of flip-flop 262. The FWD/$\overline{\text{REV}}$ signal provided by flip-flop 262 is thereby switched to a LOW logic state, causing the direction of carriage 12 to be reversed. Implicit in this reversal is the fact that carriage 12 must at some point come to a stop (i.e., have a speed of zero).

If carriage 12 is being driven in its forward direction and motor state control circuitry 164 switches the EXT LIMIT signal to a HIGH logic state, complementary output terminal $\overline{Q}$ of flip-flop 258 will be switched to a LOW logic state. This signal will be inverted by inverter 274, resulting in the application of a HIGH logic state signal to the reset terminal R of flip-flop 262. Flip-flop 262 will therefore immediately switch logic states, with the FWD/$\overline{\text{REV}}$ signal at its output terminal Q switching to a LOW logic state, thereby reversing the direction of carriage 12. Implicit in this reversal of direction is the fact that carriage 12 must at some point first come to a stop.

When carriage 12 is being driven in normal operation in its reverse direction (towards its flexion limit), the FWD/$\overline{\text{REV}}$ signal present at output terminal Q of flip-flop 262 will be at a LOW logic state. Should carriage 12 reach its preset flexion end position in normal operation, extension and flexion end detection circuitry 168 will generate a FLEX END signal having a HIGH logic state, along with a RESET signal having a HIGH logic state. The signal at complementary output terminal $\overline{\text{Q}}$ of flip-flop 256 will thereby switch to a LOW logic state. This signal will be inverted by NAND gate 272 since $\overline{\text{PWR RST}}$ will be HIGH, with a HIGH logic state signal being applied to the set terminal S of flip-flop 262. Since the reset terminal R of flip-flop 262 will be at a LOW logic state at this time, the FWD/$\overline{\text{REV}}$ signal at the output terminal Q of this flip-flop will be switched to a HIGH logic state, thereby reversing direction of carriage 12, and causing the carriage to be driven in a forward direction. Implicit in this reversal of direction is the fact that carriage 12 must at some point come to a stop.

When carriage 12 is being driven in normal operation in its reverse direction and motor state control circuitry 164 causes the FLEX LIMIT signal to switch to a HIGH logic state, flip-flop 256 will cause the signal at complementary output terminal $\overline{\text{Q}}$ to switch to a LOW logic state. This signal is inverted by NAND gate 272, resulting in a HIGH logic state signal being applied to the set terminal S of flip-flop 262. As a result, the FWD/$\overline{\text{REV}}$ signal at output terminal Q of flip-flop 262 will switch to a HIGH logic state, thereby reversing the direction of carriage 12. Implicit in this reversal of direction is the fact that carriage 12 must at some point come to a stop.

Figure 8:
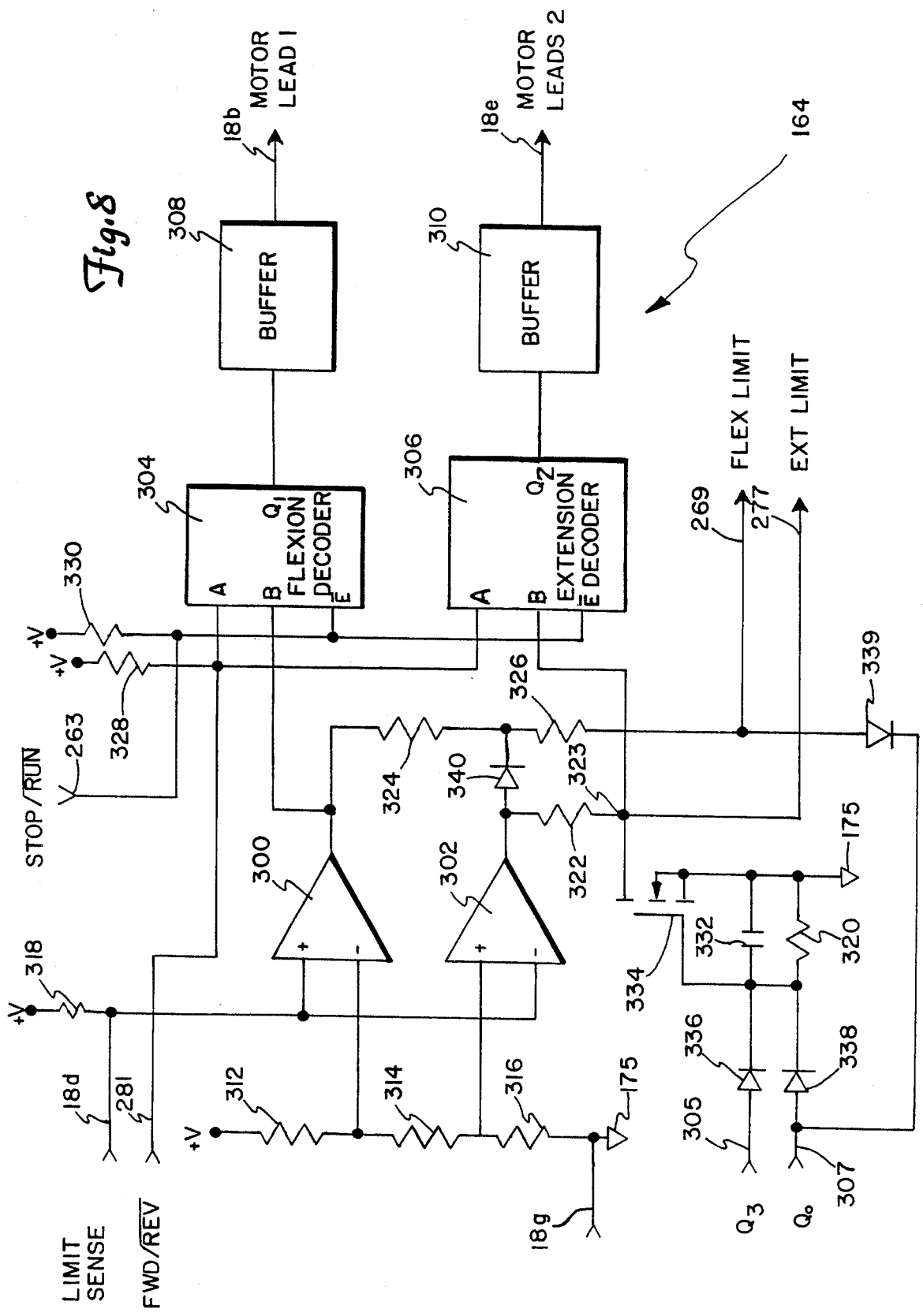
FIG. 8 is a detailed schematic diagram of the motor state control shown in FIG. 4.

Motor state control circuitry 164 is illustrated in greater detail in FIG. 8. As shown, motor state control circuitry 164 includes comparators 300 and 302, flexion decoder 304, extension decoder 306, buffers 308 and 310, resistors 312, 314, 316, 318, 320, 322, 324, 326, 328 and 330, capacitor 332, FET 334, and diodes 336, 338, 339 and 340. A non-inverting (+) input terminal of comparator 300 and an inverting (−) input terminal of comparator 302 are both connected to receive a LIMIT SENSE signal from drive unit sensing circuitry 88 over line 18d of drive cable 18, and are also connected to receive a relatively positive potential +V through pull-up resistor 318. Resistors 312, 314 and 316 are connected in series between the relatively positive potential +V and ground 175, have the same resistance value, and thereby form a voltage divider. An inverting (−) terminal of comparator 300 is connected to a node between resistors 312 and 314. A non-inverting (+) terminal of comparator 302 is connected to a node between resistors 314 and 316.

An output terminal of comparator 300 is coupled to a B input terminal of flexion decoder 304 and to an anode of diode 340 through resistor 324. An anode of diode 340 is coupled to a cathode of diode 339 through resistor 326. An anode of diode 339 is coupled to a cathode of diode 338. An output terminal of comparator 302 is coupled to a cathode of diode 340, and to node 323, a drain terminal of FET 334 and a second input terminal B of extension decoder 306 through resistor 322. A gate terminal of FET 334 is coupled to an anode of diodes 336 and 338, and to a first terminal of both capacitor 332 and resistor 320. A source terminal of FET 334 is connected to a second terminal of capacitor 332 and to resistor 320, and to ground 175. The inverting enable input terminals E of flexion decoder 304 and extension decoder 306 are both connected to receive the STOP/$\overline{\text{RUN}}$ signal from central control circuitry 162, and to relatively positive supply potential +V through pull-up resistor 330. First input terminals A of flexion decoder 304 and extension decoder 306 are both connected to receive the FWD/$\overline{\text{REV}}$ signal from central control 162, and are connected to a relatively positive potential +V through pull-up resistor 328.

Output terminal Q2 of extension decoder 306 is connected to buffer 310. Output terminal Q1 of flexion decoder 304 is connected to buffer 308. The cathode of diode 336 is connected to receive a Q3 signal from extension and flexion end detection circuitry 168 over line 305. The cathode of diode 338 is connected to receive a Q0 signal from extension and flexion end detection circuitry 168 over line 307. An active high flexion limit signal FLEX LIMIT indicative of the fact that flexion limit switch 92 (FIG. 2) has been actuated is coupled from the cathode of diode 339 over line 269. An extension limit signal EXT LIMIT indicative of the fact that extension limit switch 90 has been actuated is coupled from the drain terminal of FET 334 over line 277.

The state of drive motor 82 (FIG. 4), and therefore carriage 12, is determined by the logic state of the signals present at output terminals Q1 and Q2 of flexion decoder 304 and extension decoder 306, respectively. When signals present at both terminals Q1 and Q2 have a LOW logic state, drive motor 172 is switched to its BREAK or OFF state, and will not run. When the signal at output terminal Q1 of decoder 304 is at a LOW logic state, and the signal at output terminal Q2 of decoder 306 is at a HIGH logic state, motor 82 is switched to its FORWARD state, and will drive carriage 12 in a forward direction. When the signal at output terminal Q1 of decoder 304 has a HIGH logic state, and the signal at output terminal Q2 of decoder 306 has a LOW logic state, motor 82 is switched to its REVERSE state, and will drive carriage 12 in the reverse direction. The signal present at terminals Q1 and Q2 of decoders 304 and 306, respectively, are converted to voltage and current levels necessary to drive motor 82 by buffers 308 and 310, respectively. The signals from buffer 308 are applied to drive motor 82 through first motor lead 18b of drive unit cable 18. The signals from buffer 310 are applied to drive motor 82 over second motor lead 18e of drive unit cable 18.

As shown in FIG. 8, enable terminal E of decoders 304 and 306 are both connected to receive the STOP/$\overline{\text{RUN}}$ signal received from central control 162. Whenever the STOP/$\overline{\text{RUN}}$ signal has a HIGH logic state, output terminals Q1 and Q2 of decoders 304 and 306 will both have a LOW logic state. As a result, motor 82 will be switched to its OFF state. Whenever the STOP/$\overline{\text{RUN}}$ signal has a LOW logic state, decoders 304 and 306 are enabled, and the logic state of signals at their output terminals Q1 and Q2, respectively, are determined as a function of the signals applied to their input terminals A and B.

As discussed above, resistors 312, 314 and 316 preferably have the same resistance value, and function as a voltage divider. In one preferred embodiment, motor state control circuitry 164 is supplied with a +V potential of five volts. The potential applied to the inverting (−) input terminal of comparator 300 will be two-thirds V, or 3.3 volts. The potential applied to the non-inverting (+) terminal of comparator 302 will be one-third V, or 1.3 volts.

Drive unit sensing circuitry 88 (discussed in greater detail in subsequent portions of this specification) provides a LIMIT SENSE signal to motor state control circuitry 164 which has a potential equal to one-half V when carriage 12 and cover 14 are operating in their normal manner (i.e., switches 90, 92 and 94 are not actuated). Under the these circumstances, the signal present at the output of comparator 300 and applied to input terminal B of flexion decoder 304 will have a LOW logic state. The signal present at the output of comparator 302 and applied to the input terminal B of extension decoder 304 will also have a LOW logic state. Under these circumstances, and when the FWD/REV signal received from motor direction control circuitry 162 has a HIGH logic state, the signal present at output terminal Q1 of decoder 304 will have a LOW logic state, while the signal present at output terminal Q2 of decoder 306 will have a HIGH logic state. As a result, drive motor 82 is switched to its FORWARD state and carriage 12 driven in a forward direction. When motor direction control 162 causes the FWD/REV signal to have a LOW logic state, the signal present at output terminal Q1 of decoder 304 will have a HIGH logic state, while the signal present at output terminal Q2 of decoder 306 will have a LOW logic state. Drive motor 82 is thereby switched to its REVERSE state, and carriage 12 driven in a reverse direction.

The Q3 signal applied to diode 336 is received from extension and flexion end detection circuitry 168, and will have a HIGH logic state when carriage 12 is currently positioned at an intermediate position with an angle greater than or equal to 80° and less than 100°. When carriage 12 is at an angle less than 80° or greater than or equal to 100°, signal Q3 will have a LOW logic state. Signal Q0 is also received from extension and flexion end detection circuitry 168, and will have a LOW logic state if carriage 12 is currently positioned at an angle less than 100°, and a HIGH logic state if carriage 12 is positioned at an angle greater than or equal to 100° (i.e., almost to its maximum flexion position). If either signals Q3 or Q0 are switched to their HIGH logic state, FET 334 is turned ON, causing node 323, and therefore input terminal B of decoder 306 and the EXT LIMIT signal to be grounded or pulled to a LOW logic state.

If cover switches 94 (FIG. 3) are actuated by cover S6 as a result of pressure on the cover, or if extension limit switch 90 (FIG. 2) is actuated by crank arm 102, drive unit sensing circuitry 88 (FIGS. 4 and 9) causes the LIMIT SENSE signal applied to motor state control circuitry 164 to be switched to a LOW logic state of zero volts. If flexion limit switch 92 is actuated by crank arm 102, drive unit sensing circuitry 88 causes the LIMIT SENSE signal to be switched to a HIGH logic state. The consequences of these actions are as follows.

When the LIMIT SENSE signal received from drive unit sensing circuitry 88 is switched to a LOW logic state (i.e., one of cover switches 94 or extension limit switch 90 is actuated), and signals Q0 and Q3 are both LOW (i.e., carriage 12 is at an angle less than 80°), the output of comparator 302, and therefore node 323 and input terminal B of decoder 306, as well as the EXT LIMIT signal provided to central control 162 will be switched to a HIGH logic state. The FLEX LIMIT signal is, however, forced to remain at a LOW logic state, inhibiting action caused by actuation of flexion limit switch 92. As previously discussed, in response to the EXT LIMIT signal being switched to its HIGH state, motor direction control 162 causes the FWD/REV signal to be switched to a LOW logic state. Motor 82 will thereby be switched to its REVERSE state by motor state control circuitry 164, and drive carriage 12 in the reverse direction towards its flexion end position.

When carriage 12 is being driven in such a manner that it is positioned at an angle greater than or equal to 80° but less than 100°, the Q3 signal received from extension and flexion end detection circuitry 168 will be HIGH, while the Q0 signal will be LOW. FET 334 is thereby switched ON, forcing the EXT LIMIT signal to remain in its LOW logic state.

The actuation of one of cover switches 94 or extension limit switch 90 will thereby have no effect. Since the Q0 signal is also low, the FLEX LIMIT signal is forced LOW, and actuation of flexion limit switch 92 will have no effect either.

When carriage 12 is positioned at an angle greater than or equal to 100°, the Q3 output signal from extension and flexion end detection circuitry 168 will be at a LOW logic state, while the Q0 output signal will be at a HIGH logic state. FET 334 will thereby be switched to its ON state, forcing the EXT LIMIT signal to a LOW logic state to inhibit action which could be caused by actuation of extension limit switch 90. Should flexion limit switch 92 be actuated at this time, the output of comparator 300 will switch to a HIGH logic state, thereby causing the FLEX LIMIT signal to switch to a HIGH logic state. In response, the FWD/REV signal provided by central control 162 will be switched to a HIGH logic state. Motor state control 164 will thereby be switched to its FORWARD state and drive carriage 12 in its forward direction toward its extension end position. If one of cover switches 94 is actuated, the output of comparator 302 is switched HIGH. This action will cause the FLEX LIMIT signal to switch HIGH with the same consequences (i.e., carriage 82 reversed and driven forward).

Figure 9:
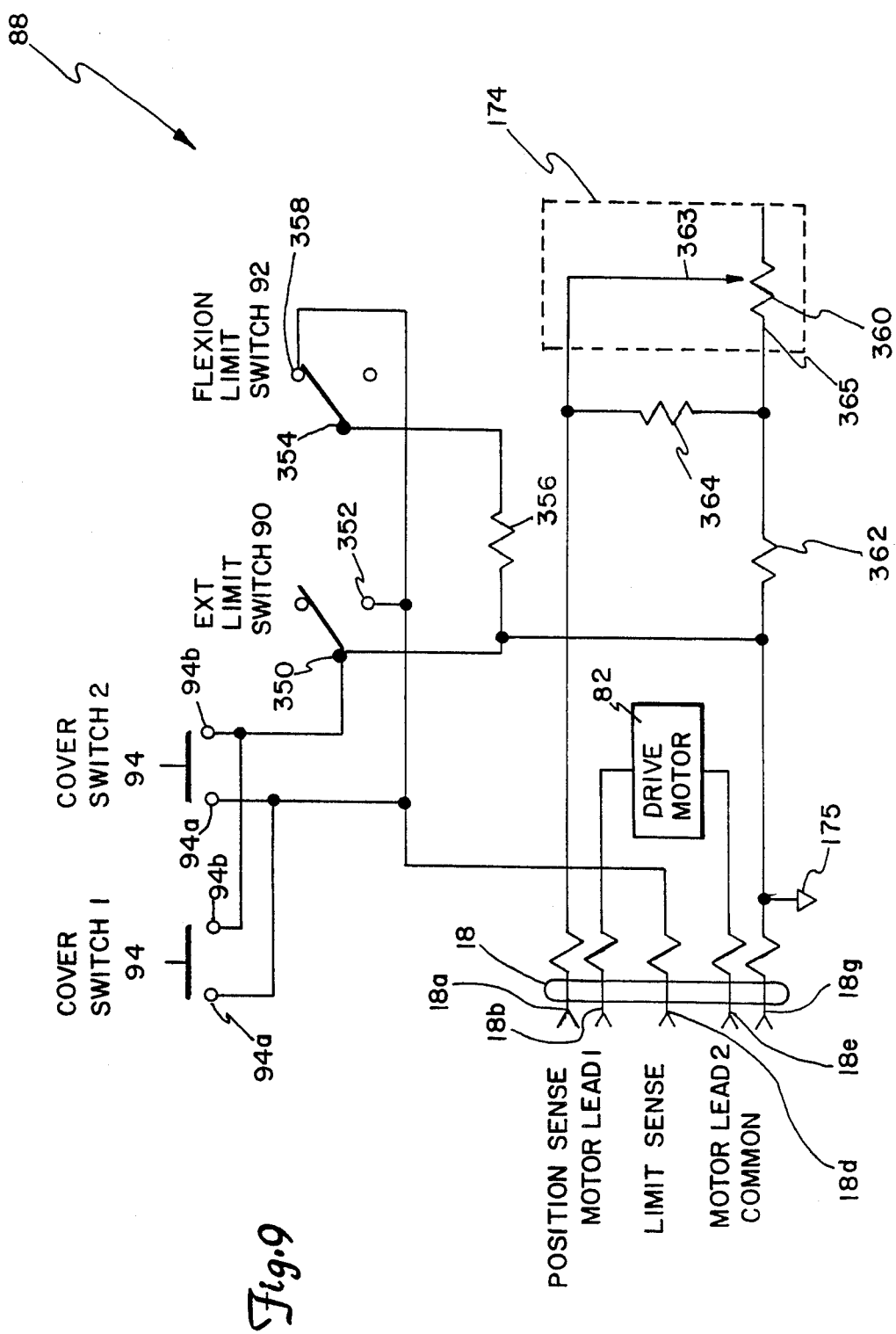
FIG. 9 is a detailed schematic diagram of drive unit sensing circuitry shown in FIG. 4.

Drive unit sensing circuitry 88 and drive motor 82 are illustrated in greater detail in FIG. 9. As shown, drive unit cable 18 includes a first lead 18a through which a POSITION SENSE signal is coupled to extension and flexion end detection circuitry 168, first motor lead 18b through which the first motor drive signal is applied to drive motor 82, lead 18d through which a LIMIT SENSE signal is coupled to motor state control 164, second motor lead 18e through which the second motor drive signal is provided to drive motor 82, and lead 18g which is coupled to ground 175.

Cover switches 94 are both normally open as shown in FIG. 9, and coupled in parallel, both having a terminal 94a connected to lead 18d and a terminal 94b connected to lead 18g. Extension limit switch 90 is shown in its normally open position, has a first terminal 350 coupled to lead 18g, and a second terminal 352 connected to lead 18d. Flexion limit switch 92 is shown in its normally closed position, has a first terminal 354 connected to lead 18g through resistor 356, and a second terminal 358 connected to lead 18d.

Carriage state sensor 174 includes potentiometer 360 which has its wiper arm 363 connected to a lead 18a, and a second terminal 365 connected to lead 18g through resistor 362. Wiper arm 363 and terminal 365 of potentiometer 360 are also coupled by resistor 364. Carriage state sensor 174 is mounted to forward support link 76A and drag link 78A in such a manner that wiper arm 363 will move and change the resistance of potentionmeter 360 between the wiper arm and terminal 365 as a function of the current position or angle of carriage 12. Resistors 362 and 364 function as a voltage divider along with resistor 382 of extension and flexion end detection circuitry 88 shown in FIG. 10. A POSITION SENSE signal representative of the angle of carriage 12 is provided to extension and flexion end detection circuitry over line 18a.

Resistor 356 preferably has a resistance equal to that of pull-up resistor 318 of motor state control circuitry 164 (FIG. 8). As a result, when cover switches 94, extension limit switch 90, and flexion limit switch 92 are not actuated (i.e., cover switches 94 and extension limit switch 90 in their normal open position, and flexion limit switch 92 in its normal closed position) resistors 318 and 356 function as a voltage divider causing the LIMIT SENSE signal to have a potential equal to one-half that of the +V potential applied to resistor 318. Should either of cover switches 94 or extension limit switch 90 be actuated, lead 18d will be coupled directly to lead 18g, causing the LIMIT SENSE signal to switch to a ground potential or LOW logic state. Should flexion limit switch 92 be actuated, lead 18d will float. Pull-up resistor 318 will then cause the LIMIT SENSE signal to switch to a HIGH logic state.

Figure 10:
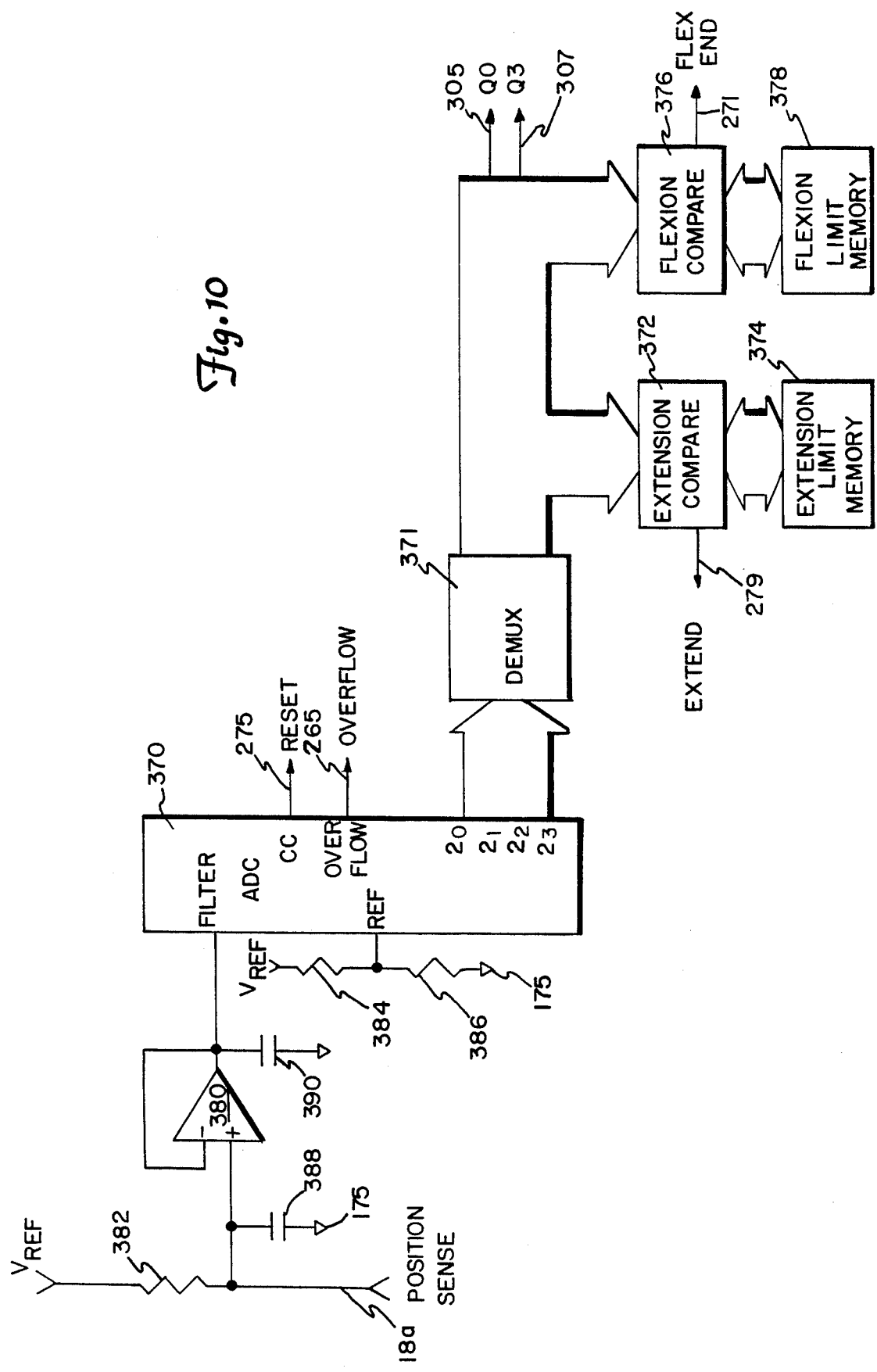
FIG. 10 is a detailed schematic diagram of the extension and flexion end detention circuitry shown in FIG. 4.

Extension and flexion end detection circuitry 168 is illustrated in greater detail in FIG. 10. As shown, extension and flexion end detection circuitry 168 includes an analog-to-digital converter (ADC) 370, demultiplexor 371, extension comparator 372, extension limit memory 374, flexion comparator 376, flexion limit memory 378, operational amplifier 380, resistors 382, 384 and 3S6, and capacitors 388 and 390.

A non-inverting (+) input terminal of operational amplifier 380 is connected to receive a reference potential $V_{REF}$ through resistor 382, and to receive the POSITION SENSE signal over lead 18a of drive unit cable 18. Reference potential $V_{REF}$ is produced by a reference voltage source (not shown) of known configuration. The non-inverting input terminal is also conncected to ground 175 through capacitor 388. An inverting (−) input terminal of operational amplifier 380 is connected to its output terminal, to ground 175 through capacitor 390, and to a FILTER input of analog-to-digital converter (ADC) 370.

Resistors 384 and 386 are connected in series between reference potential $V_{REF}$ and ground 175, and function as a voltage divider to provide a voltage potential representative of a maximum angle to which ADC 370 can provide a scaled or linear output (199° in the embodiment described herein). This potential is applied to the REF input terminal of ADC 370. The $2_0$-$2_3$ output terminals of ADC 370 are coupled to demultiplexor 371. Digital signals representative of carriage state from ADC 370 are converted to binary coded decimal (BCD) representations of carriage state by demultiplexor 371, and applied to extension comparator 372 and flexion comparator 376. Comparator 372 is also connected to receive BCD signals from extension limit memory 374 representative of a preselected extension limit. Similarly, flexion comparator 376 is connected to receive BCD signals from flexion limit memory 378 representative of a preselected flexion limit. The extension and flexion limits can be selected, and data representative thereof stored, in accordance with the system disclosed in applicant's copending application entitled LIVE DISPLAY APPARATUS FOR SETTING EXTENSION AND FLEXION LIMITS IN CONTINUOUS PASSIVE MOTION (CPM) SYSTEM, filed Dec. 20, 1985 and assigned Ser. No. 811,636.

The Q0 bit from demultiplexor 371 switches from a logic LOW to a logic HIGH state when carriage 12 is driven to an angle of 80°, and returns to the logic LOW state when carriage 12 is driven to a state of 100°. The Q3 bit from demultiplexor 371 switches from a logic LOW to a logic HIGH state when carriage 12 reaches an angle of 100°. The Q0 and Q3 signals from demultiplexor 371 are coupled to motor state control 164 over lines 305 and 307, respectively.

The POSITION SENSE signal received from drive unit sensing circuitry 88 is buffered by operational amplifier 380 before being applied to the FILTER input of ADC 370. The signal applied through the FILTER input is representative of the actual position or angle of carriage 12. ADC 370 converts this analog signal to a digital signal at its output terminals $2_0$-$2_3$ which are representative of the actual angle of carriage 12. These digital signals are then converted into BCD form as discussed above by demultiplexor 371. Each time a conversion is completed by ADC 370, RESET signal coupled from the conversion complete (CC) terminal switches to a LOW logic state, and switches back to a HIGH logic state when the next conversion begins.

The voltage applied to the REF input terminal of ADC 370 is scaled in such a manner that when carriage 12 reaches an angle of 100° or above, the Q0 output terminal of demultiplexor 371 will switch to a HIGH logic state. If carriage 12 has an angle greater than or equal to 80° yet less than 100°, the Q3 terminal of demultiplexor 371 will have a HIGH logic state. The Q0 and Q3 signals are supplied to motor state control circuitry 164 as previously discussed.

If at any time the signal input to the FILTER terminal of ADC 370 should have a potential greater than that applied to the REF input terminal, the OVERFLOW signal provided by the OVERFLOW output terminal of ADC 370 will switch to a HIGH logic state. The OVERFLOW signal is coupled to central control circuitry 162 over line 265. Central control circuitry 162 will then cause the STOP/$\overline{RUN}$ signal to switch to a logic LOW state as previously discussed. This will result in motor state control 164 switching to its OFF state, thereby halting motion of carriage 12. This action will occur if wiper terminal 363 is open circuited, or if lead 18a of drive unit cable 18 is open circuited.

Extension limit memory 374 and flexion limit memory 378 store digital data representative of preset extension and flexion limit positions, respectively, as previously discussed. Extension comparator 372 compares the data representative of the current carriage angle to that representative of the preset extension limit. When carriage 12 reaches the preset extension limit, comparator 372 produces an EXT END signal which switches to a logic HIGH state representative of this occurence. In a similar manner, flexion comparator 376 compares data representative of the current state of carriage 12 to that representative to the preset flexion limit. When carriage 12 is driven to its preset flexion limit, flexion comparator 376 produces a FLEX END signal which switches to a HIGH logic state.

If either lead 18a or 18g of cable 18 were to fail and open circuit, the POSITION SENSE signal applied to extension and flexion end detection circuitry 168 would float, causing the OVERFLOW signal to switch to a HIGH logic state. Motor 82 will then be switched to its OFF state and motion of carriage 12 stopped.

Although the present invention has been described with reference to the preferred embodiments, those skilled in the art will recognize that changes may be made in form and detail without departing from the spirit and scope of the invention.

What is claimed is:

1. A continuous motion system for providing continuous motion therapy to a patient's limb, including:
   a carriage for supporting a patient's limb;
   drive means for driving the carriage through a range of reciprocal angular movement;
   neuromuscular stimulation (NMS) means for applying electrical stimulation to muscles of the patient's limb; and
   control means for controlling the drive means and the NMS means, the control means including:
      ON/OFF switch means having ON and OFF states for controlling the application of power to the control means;
      NMS switch means having ON and OFF states for controlling the NMS means; and
      NMS safety circuit means coupled to the ON/OFF switch means, the NMS switch means and the NMS means for disabling the NMS means and thereby preventing the application of electrical stimulation when the ON/OFF switch means is is in its ON state until after the NMS switch means has been switched from its OFF state to its ON state.

2. The continuous motion system of claim 1 wherein:
   the NMS means includes: enable input means for receiving an enable signal; and
   the NMS safety circuit means includes:
      power-up reset means coupled to the ON/OFF switch means for providing a power reset signal when the ON/OFF switch means is switched from its OFF state to its ON state; and
      latch means coupled between the power-up reset means, the NMS switch means and the enable input means of the NMS means, for providing the enable signal only after receiving the power reset signal and after the NMS switch means is in its OFF state.

3. The continuous motion system of claim 1 wherein:
   the NMS means includes:
      first channel NMS means for applying electrical stimulation to muscles of the patient's limb at a first location;
      second channel NMS means for applying electrical stimulation to muscles of the patient's limb at a second location;
   the NMS switch means includes:
      first channel NMS switch means having ON and OFF states for controlling the first channel NMS means:
      second channel NMS switch means having ON and OFF states for controlling the second channel NMS means; and
   the NMS safety circuit means is coupled to the first and second channel NMS means and the first and second channel NMS switch means and disables the first and second channel NMS means and thereby prevents the application of electrical stimulation by either the first or second channel NMS means when the ON/OFF switch means is in its ON state until after both the first and second channel NMS switch means have been switched from their OFF state to their ON state.

4. A continuous motion system for providing continuous motion therapy to a patient's limb, including:
   a carriage for supporting a patient's limb;
   drive unit means for driving the carriage through a range of reciprocal angular movement by cyclically driving the carriage in a first direction toward an extension end position and in a second direction toward a flexion end position;
   obstruction sensor means for sensing obstructions with respect to the carriage; and
   control means responsive to the obstruction sensor means for controlling the drive unit means and causing the carriage to be driven as a function of sensed obstructions.

5. The continuous motion system of claim 4 wherein the drive unit means is positioned adjacent the carriage and the obstruction sensor means senses obstructions between the carriage and drive unit means.

6. The continuous motion system of claim 5 wherein:
   the drive unit means is positioned below the carriage; and
   the sensor means includes:
      a cover over the drive unit means;
      pivot means for pivotally mounting the cover over the drive unit means; and
      cover switch means coupled to the control means for sensing pressure exerted on the cover by obstructions between the carriage and cover.

7. The continuous motion systen of claim 6 wherein the cover switch means includes a plurality of cover switches mounted with respect to the cover at spaced-apart locations and coupled to the control means in a parallel circuit, for sensing pressure exerted at different locations of the cover.

8. The continuous motion system of claim 6 wherein the sensor means further includes bias means for biasing the cover to a position at which the cover switch means are not actuated.

9. The continuous motion system of claim 4 wherein:
   the system further includes carriage state sensor means for sensing carriage state within its range of reciprocal angular movement; and
   the control means is coupled to the carriage state sensor means and causes the carriage to be driven in the second direction when an obstruction is sensed and the carriage is within a first portion of its range of reciprocal angular movement.

10. The continuous motion system of claim 9 wherein the control means causes the carriage to be driven in the second direction when an obstruction is sensed and the carriage is within a first portion of its range of reciprocal angular movement ovement adjacent the extension end position.

11. The continuous motion system of claim 9 wherein the control means causes the carriage to be driven in the first direction when an obstruction is sensed and the carriage is within a second portion of its range of reciprocal angular movement.

12. The continuous motion system of claim 11 wherein the control means causes the carriage to be driven in the first direction when an obstruction is sensed and the carriage is within a second portion of its range of reciprocal angular movement adjacent the flexion end position.

13. The continuous motion system of claim 11 wherein the control means causes the carriage to continue to be driven in the direction in which it is being driven when an obstruction is sensed and the carriage is within a third portion of its range of reciprocal angular movement which is between the first and second portions of the range.

14. The continuous motion system of claim 4 wherein:
   the system further includes carriage state sensor means for sensing carriage state within a first portion of the range of angular movement which is adjacent to the extension end position, a second portion of the range of angular movement which is adjacent to the flexion end position, and a third position of the range of angular movement which is between the first and second portions; and
   the control means is coupled to the carriage state sensor means and causes the carriage to be driven in the second direction when carriage state is within the first portion of the range of angular movement when an obstruction is sensed, to be driven in the first direction when carriage state is within the second portion of the range of angular movement when an obstruction is sensed, and to continue to be driven in the direction in which it is being driven when carriage state is within the third portion of the range of angular movement when an obstruction is sensed.

15. The continuous motion system of claim 4 and further including:
   flexion limit switch means coupled to the control means and mounted with respect to the drive unit means for sensing a first physical characteristic of the drive unit means when the carriage has been driven to a predetermined flexion limit position, wherein the control means causes the carriage to be driven in the first direction when the first physical characteristic of the drive unit means is sensed; and
   extension limit switch means coupled to the control means and mounted with respect to the drive unit means for sensing a second physical characteristic of the drive unit means when the carriage has been driven to a predetermined extension limit position, wherein the control means causes the carriage to be driven in the second direction when the second physical characteristic of the drive unit means is sensed.

16. The continuous motion system of claim 15 wherein:
   the drive unit means includes: a drive motor; and
   a crank arm coupling the drive motor to the carriage;
   the flexion limit switch means is mounted with respect to the drive unit means to sense the crank arm when the carriage is driven to the extension limit position; and
   the extension limit switch means is mounted with with respect to the drive unit means to sense the crank arm when the carriage is driven to the extension limit position.

17. A continuous motion system for providing continuous motion therapy to a patient's limb, including:
   a carriage for supporting a patient's limb;
   drive unit means for driving the carriage through a range of reciprocal angular movement;
   a remote patient controller switch;
   a remote patient controller cable having a plurality of conductors with first and second ends, the first ends of the conductors interfaced to the remote patient controller switch; and
   control means, to which the second ends of the conductors of the remote patient controller cable are interfaced, for controlling the drive unit means as a function of patient actuation of the remote patient controller switch and for causing motion of the carriage to stop when some of the conductors of the remote patient controller cable are open circuited.

18. The continuous motion system of claim 17 wherein the control means causes motion of the carriage to stop when another of the conductors of the remote patient controller cable is open circuited and the remote patient controller switch is actuated.

19. The continuous motion system of claim 18 wherein:
   the remote patient controller switch includes:
      first, second and third terminals;
      a contact member for selectively interconnecting the first terminal to one of the second and third terminals; and
      bias means for biasing the contact member to interconnect the first and second terminals when the contact member is unactuated;
   the remote patient controller cable includes first, second and third conductors having first ends interconnected to the first, second and third terminals, respectively, of the remote patient controller switch and second ends; and
   the control means is connected to receive the second ends of the first, second and third conductors of the remote patient controller cable and causes motion of the carriage to stop when either of the first or second conductors is open circuited, or when the third conductor is open circuited and the contact member of the remote patient controller switch is actuated.

20. A continuous motion system for providing continuous motion therapy to a patient's limb, including:
   a carriage for supporting a patient's limb;
   drive unit means for driving the carriage through a range of reciprocal angular movement;
   a remote patient controller switch;
   a remote patient controller cable having a plurality of conductors with first and second ends, the first ends of the conductors interfaced to the remote patient controller switch; and
   control means, to which the second ends of the conductors of the remote patient controller cable are interfaced, for controlling the drive unit means as a function of patient actuation of the remote patient controller switch and for causing motion of the carriage to stop when some of the conductors of the remote patient controller cable are short circuited to one another.

21. The continuous motion system of claim 20 wherein the control means causes motion of the carriage to stop when another of the conductors of the remote patient controller cable is short-circuited to another of the conductors and the remote patient controller switch is actuated.

22. The continuous motion system of claim 21 wherein:
   the remote patient controller switch includes:
      first, second and third terminals;
      a contact member for selectively interconnecting the first terminal to one of the second and third terminals; and bias means for biasing the contact member to interconnect the first and second terminals when the contact member is unactuated;

the remote patient controller cable includes first, second and third conductors having fist ends interconnected to the first, second and third terminals, respectively, of the remote patient controller switch and second ends; and the control means is connected to receive the second ends of the first, second and third conductors of the remote patient controller cable and causes motion of the carriage to stop when either of the first or second conductors are shorted together and the contact member of the remote patient controller switch is actuated.

23. A continuous motion system for providing continuous motion therapy to a patient's limb, including:

a carriage for supporting a patient's limb;

drive unit means for driving the carriage through a range of reciprocal angular movement;

a remote patient controller switch;

a remote patient controller cable having a plurality of conductors with first and second ends, and first ends of the conductors interfaced to the remote patient controller switch;

a plug connector interfaced to the second ends of the conductors of the remote patient controller cable; and control means, including a jack adapted to receive the plug connector, for controlling the drive unit means as a function of patient actuation of the remote patient controller switch and for causing motion of the carriage to stop when the plug connector is unplugged from the jack.

24. The continuous motion system of claim 23 wherein the controller means causes motion of the carriage to stop when the plug connector is plugged into the jack.

* * * * *

UNITED STATES PATENT AND TRADEMARK OFFICE
CERTIFICATE OF CORRECTION

PATENT NO. : 4,798,197

DATED : January 17, 1989

INVENTOR(S) : Robert H. Nippoldt et al.

It is certified that error appears in the above-identified patent and that said Letters Patent is hereby corrected as shown below:

Col. 20, line 54, delete "overment" and insert --movement--.

Col. 24, line 5, delete "and" (second occurrence) and insert --the--.

Signed and Sealed this

Twenty-eighth Day of November 1989

Attest:

JEFFREY M. SAMUELS

Attesting Officer     Acting Commissioner of Patents and Trademarks